(12) United States Patent
Manneschi

(10) Patent No.: US 7,442,935 B2
(45) Date of Patent: Oct. 28, 2008

(54) DEVICE FOR ANALYZING THE COMPOSITION OF THE CONTENTS OF A CONTAINER

(76) Inventor: Alessandro Manneschi, 15, via XXV Aprile, I-52100 Arezzo (IT)

( * ) Notice: Subject to any disclaimer, the term of this patent is extended or adjusted under 35 U.S.C. 154(b) by 0 days.

(21) Appl. No.: 11/404,214

(22) Filed: Apr. 14, 2006

(65) Prior Publication Data

US 2006/0255276 A1   Nov. 16, 2006

(30) Foreign Application Priority Data

Apr. 15, 2005 (FR) ................................. 05 03774
Jul. 19, 2005 (FR) ................................. 05 07643

(51) Int. Cl.
*G01J 5/34* (2006.01)
(52) U.S. Cl. .................. 250/339.12; 324/228; 324/639
(58) Field of Classification Search ............ 250/339.12; 324/445, 226, 228, 442, 639
See application file for complete search history.

(56) References Cited

U.S. PATENT DOCUMENTS

| | | | |
|---|---|---|---|
| 3,609,526 A | 9/1971 | Chaberski | |
| 4,220,915 A | 9/1980 | Kawawmoto et al. | |
| 4,403,191 A | 9/1983 | Satake | |
| 5,514,337 A | 5/1996 | Groger et al. | |
| 6,028,433 A | 2/2000 | Cheiky-Zelina et al. | |
| 6,511,851 B1 | 1/2003 | Payne et al. | |
| 2003/0222662 A1 | 12/2003 | Geisel | |
| 2004/0174154 A1 | 9/2004 | Butters | |

FOREIGN PATENT DOCUMENTS

FR   2 815 718   4/2002

*Primary Examiner*—David P. Porta
*Assistant Examiner*—Mark R Gaworecki
(74) *Attorney, Agent, or Firm*—Blakely, Sokoloff, Taylor & Zafman LLP

(57) ABSTRACT

The present invention relates to a device for analyzing the composition of the contents of a receiver comprising: means (40) for emitting/receiving an electromagnetic field at a variable frequency over a determined frequency range, means (22) for supporting a container (R), the contents of which should be analyzed, adapted in order to provide relative accurate positioning between the emitting/receiving means (40) and the container (R), means (50) capable of measuring the complex impedance of the emitting/receiving means influenced by the load formed by the container (R) and its contents, representative of the complex dielectric characteristics of the container and of its contents, and means (50) capable or providing a piece of information related to the measured complex impedance and consequently to the nature of the contents of said container.

56 Claims, 5 Drawing Sheets

Figure 1:
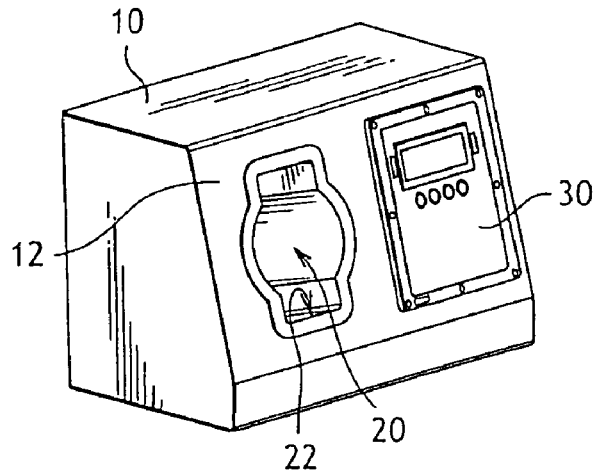

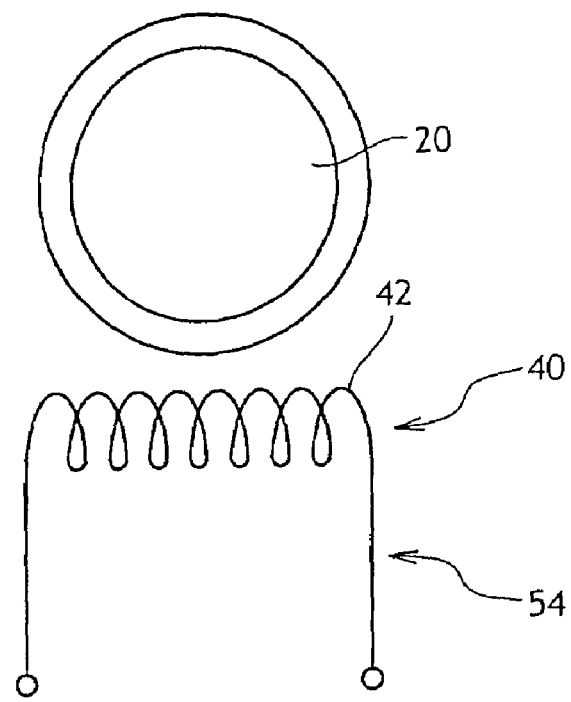
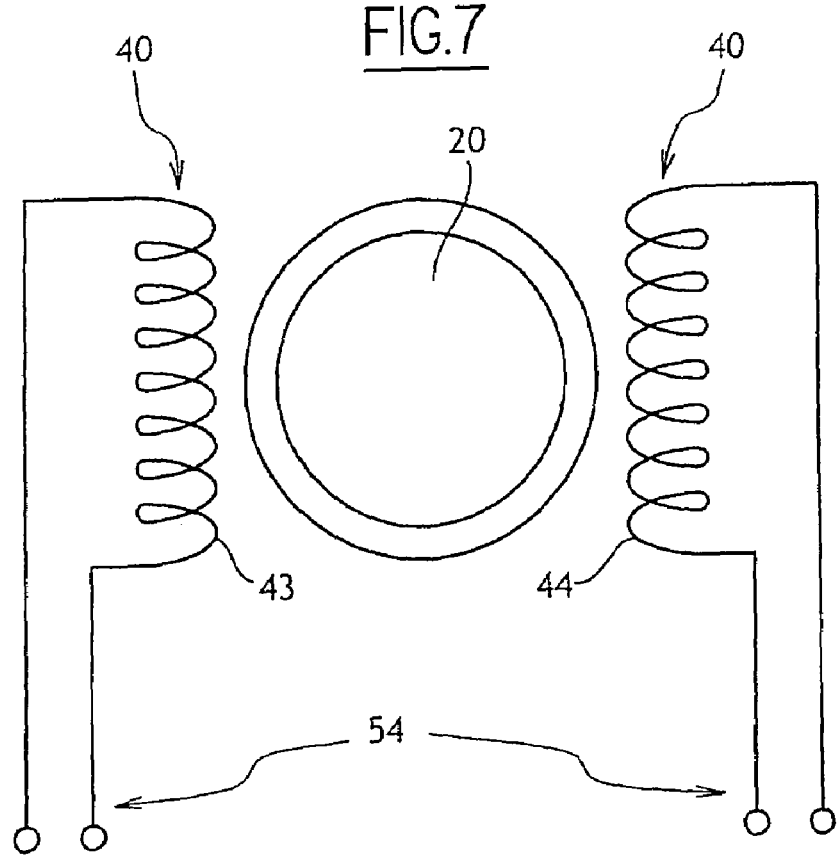

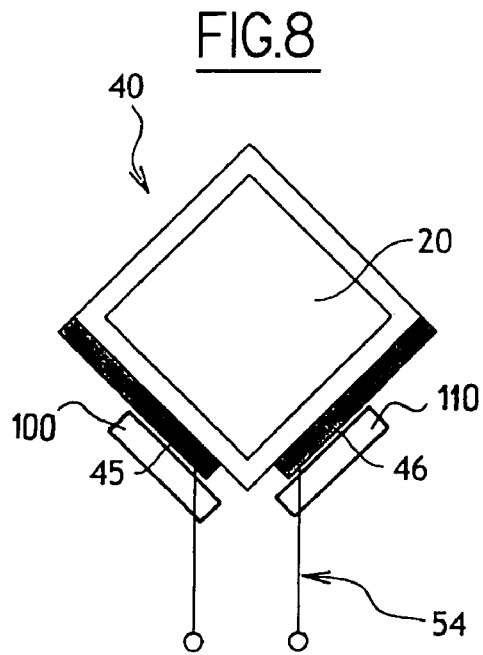
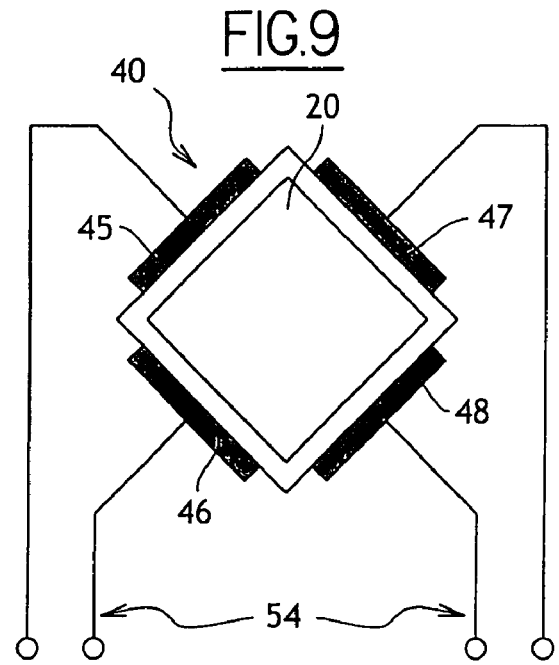
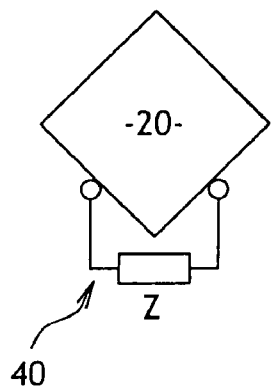
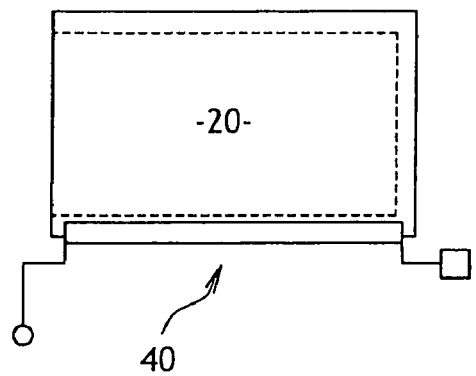
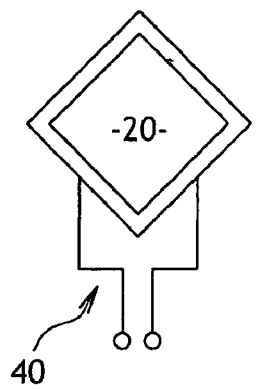
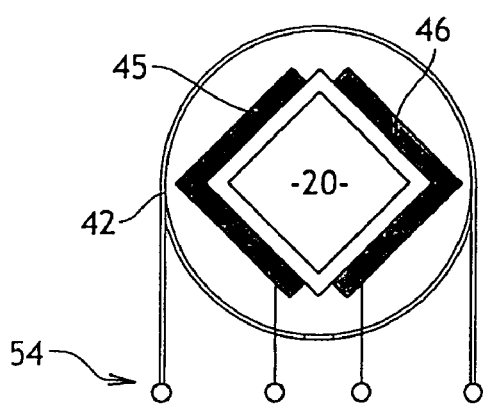
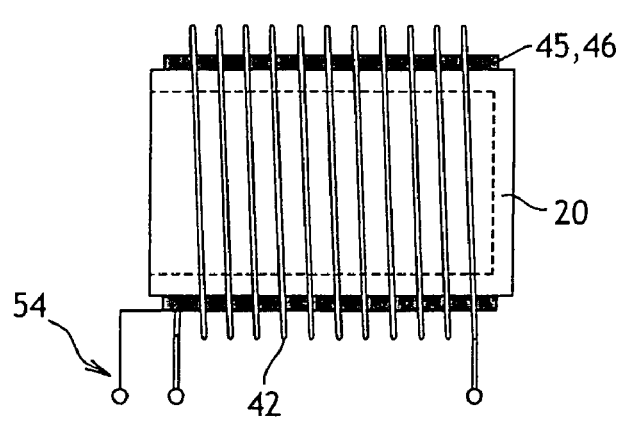

DEVICE FOR ANALYZING THE COMPOSITION OF THE CONTENTS OF A CONTAINER

The present invention relates to the field of analyzing the composition of contents of containers such as bottles;

The present invention may find many applications. It may notably be applied to control of manufacturing in bottling factories in order to avoid any tampering on the contents of the containers subsequently provided to the general public. The invention may also be applied to controlling luggage transported by passengers in particular hand luggage kept by passengers in airports.

With the well-known X ray examination means, it is not possible to determine the contents of bottles or equivalent containers. Such examination means indeed only provide classification into two categories, organic materials and inorganic materials. With them, it is not possible to distinguish two organic materials from each other.

Moreover, sealed plastic or glass bottles do not allow their contents to be sampled and therefore do not allow the latter to be analyzed except by performing a forced opening.

Finally, the hitherto suggested means for attempting to proceed with analysis of the contents of the containers require complex handling of the latter.

In this situation, a substantial need is perceived, for having simple, quick and easily applied non-destructive means of investigation in order to determine the composition of the contents of the containers.

This object is achieved within the scope of the present invention by a device for analyzing the composition of the contents of a container comprising:

- a channel for receiving a container on the one hand, said receiving channel is defined by generatrices tilted downwards away from the open front face of the channel through which a container is introduced, and
- non-destructive analysis means associated with this channel, on the other hand.

As it will be understood upon reading the following description, by using a receiving channel defined by generatrices tilted downwards away from the open front face of the channel through which a container is introduced, it is possible to very accurately and very quickly position the containers relatively to the detection means. Indeed, it is sufficient to let the container slide against a channel bottom, opposite to its open front face in order to automatically position the container. The present invention thus guarantees both reliable detection and fast throughput at the control level.

Preferably within the scope of the present invention, the non-destructive analysis means comprise:

- means for emitting/receiving an electromagnetic field at least at several frequencies comprised in a determined frequency range,
- means capable of measuring the complex impedance of the emitting/receiving means influenced by the load formed by the container and its contents, representative of the complex dielectric characteristics of the container and of its contents, and
- means capable of providing a piece of information related to the measured complex impedance and consequently to the nature of the contents of said container.

Within the scope of the present invention, by << at least several frequencies >> is meant a number of frequencies larger than 1.

According to another advantageous feature of the present invention, the means capable of providing a piece of information related to the measured complex impedance and consequently to the nature of the contents of said container, comprise means capable of comparing the measured complex impedance with predetermined reference values for the same frequency range and generating an alarm, when the measured complex impedance deviates from the reference values.

According to another advantageous feature of the present invention, the means capable of providing a piece of information related to the measured complex impedance comprise means capable of indicating the thereby detected nature of the contents of the container or at least the family of these contents.

Figure 3:
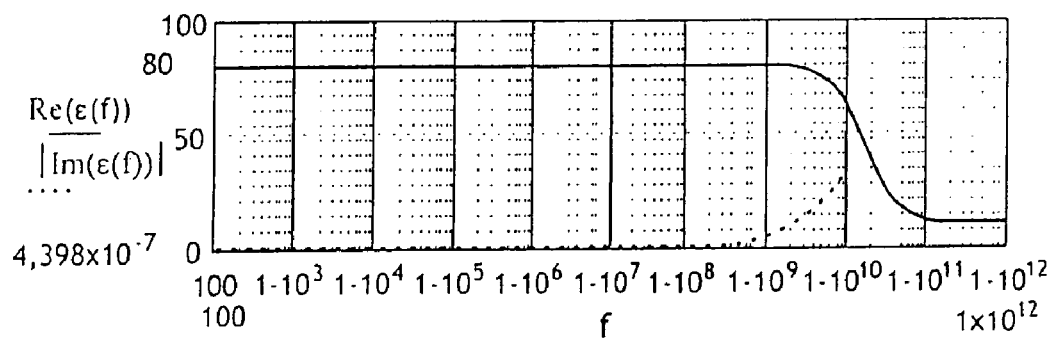
Figure 4:
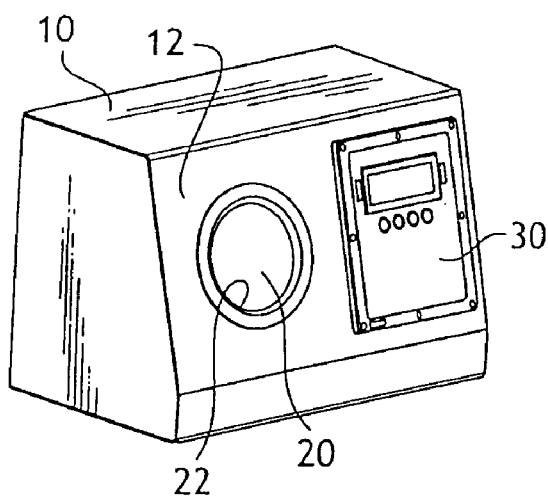
Figure 5:
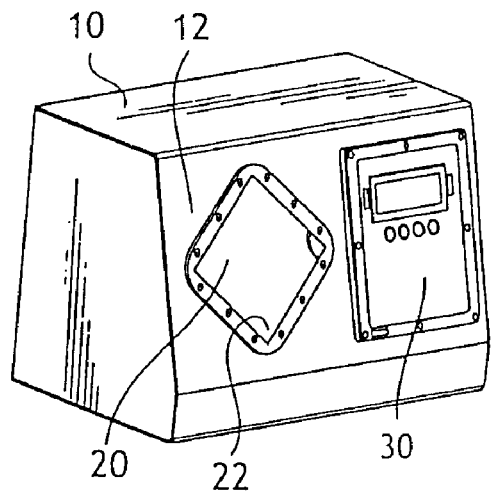
Figure 2:
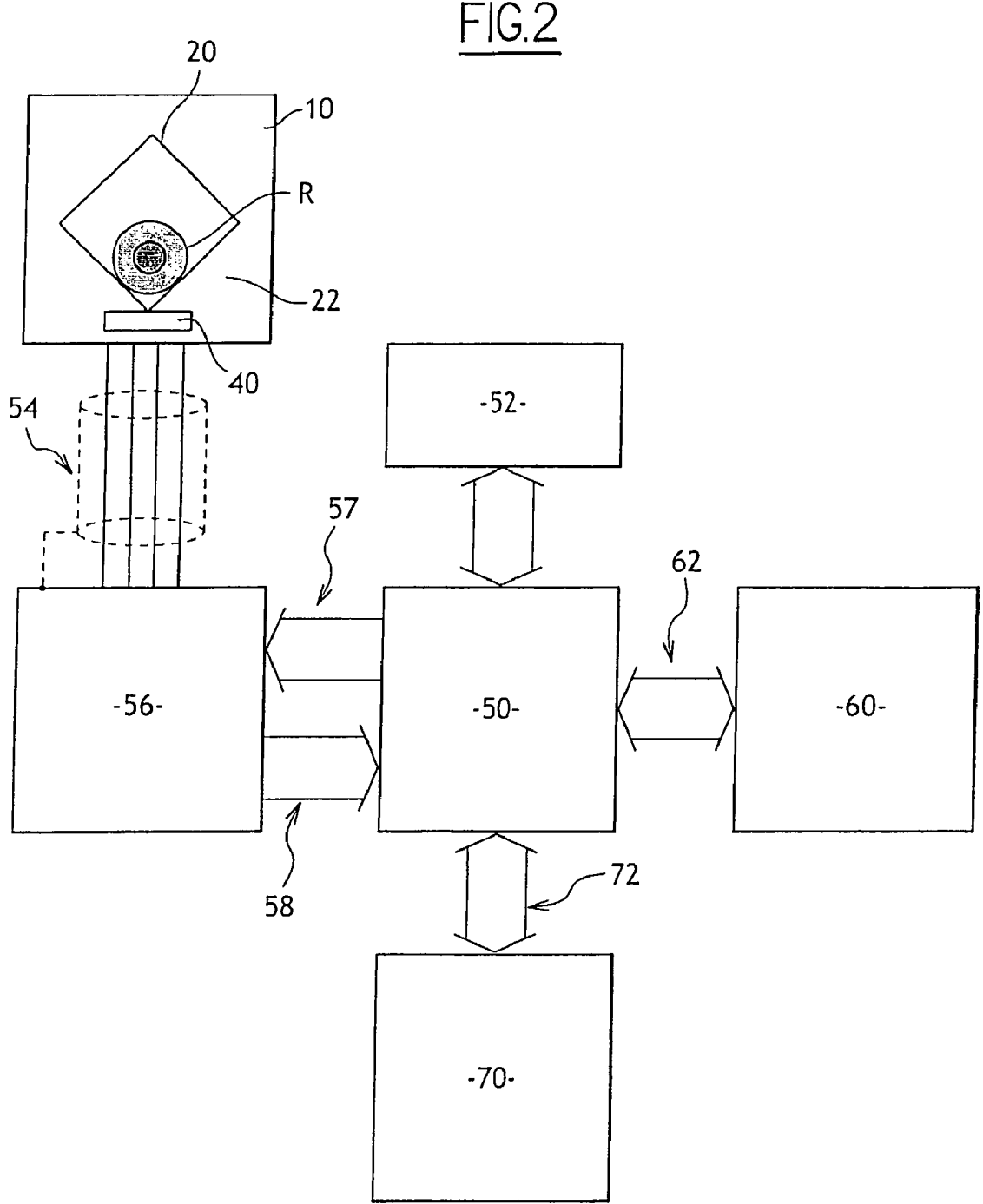

Other features, objects and advantages of the present invention will become apparent upon reading the detailed description which follows, and considering the appended drawings, given as non-limiting examples and wherein:

FIG. 1 illustrates a schematic perspective view of an analysis device according to a first embodiment of the present invention, FIG. 2 illustrates a schematic view as functional blocks of the essential components making up this device, FIG. 3 illustrates the real part and the imaginary part of the measured complex impedance in the case of a load consisting of water, over a large frequency range, FIGS. 4 and 5 illustrate two schematic perspective views of alternatives of the device illustrated in FIG. 1, FIGS. 6, 7 8 and 9 illustrate four alternative embodiments of emitting/receiving electromagnetic sensors according to the present invention, and FIGS. 10a, 10b and 10c illustrate a fifth alternative embodiment, whereas FIGS. 11a and 11b illustrate a sixth alternative embodiment of emitting/receiving electromagnetic sensors according to the present invention, FIGS. 12a and 12b, and 13a and 13b illustrate alternative embodiments of the invention used for analyzing containers with variable volumes.

The applied measuring means within the scope of the preferred embodiment of the present invention are essentially based on the following approach.

Dielectric materials have four basic polarizations: electronic, ionic, dipole and migrational polarizations.

Each type of polarization is characterized by a setting-up time, called rise time. If the excitation electromagnetic field has a pulsation larger than the reciprocal of the rise time, polarization cannot be achieved. Consequently, polarization is only present at frequencies less than the cut-off frequencies and is absent for higher frequencies. In the transition zone, a phenomenon of energy loss occurs in the dielectric due to the rotation of molecules out of phase with respect to the excitation field.

The rise times for electronic polarization are from $10^{-14}$ to $10^{-15}$ s, i.e., in the optical domain. Such a frequency range is difficult to utilize on an industrial scale as the bottles to be examined may frequently be partly or completely opaque.

Ionic polarization has rise times between $10^{-13}$ and $10^{-14}$ s, very close to electron relaxation times. It is therefore also difficult to utilize them.

Dipole polarization is characteristic of polar dielectrics (as water for example).

Dipole polarization, unlike electronic and ionic polarizations which are inertialess, persists for a certain time after extinction of an excitation. Dipole polarization decreases with an exponential law and a time constant, called the relaxation time, between $10^{-6}$ and $10^{-11}$ s, i.e., in the radiofrequency domain. Electromagnetic waves having these frequencies may pass through glass, plastic and other dielectric materials. The applicant thus determined that electromagnetic waves may be used for examining the contents of bottles or equivalent containers.

Migrational polarization is present in certain dielectrics, in particular in heterogeneous materials which contain impurities. In this case, the charges move very slowly and the rise time may be of several seconds, minutes, or even sometimes hours. This polarization time is therefore only measurable at very low frequency.

Water which is a polar liquid, and therefore water-based liquids, have a relaxation time of the order of $10^{-11}$ s at room temperature, corresponding to a frequency of 16 GHz. Measurement of the complex dielectric constant at a lower frequency than that of the relaxation frequency shows a high real part and limited losses (distilled water) as illustrated in the appended FIG. 3.

Saturated hydrocarbons $C_nH_{(2n+2)}$ are non-polar molecules and with a very low electric dipole moment, for example they do not exhibit a dipole polarization phenomenon and the value of the real part of the dielectric constant is low (relative dielectric constant of the order of 2). Losses in hydrocarbons are insignificant up to very high frequencies. If a hydrocarbon molecule loses its symmetry such as for example in the case of ethyl or methyl alcohol, an electric dipole moment and consequently a constant larger than the one obtained in the case of hydrocarbons and a resonance phenomenon at the dipolar relaxation frequency appear.

The physical phenomena described above are known since the end of the 30s (see for example Peter Debye Nobel Lecture, 1936).

However, they have not been applied up to now for efficiently analyzing the contents of containers.

The casing of an analysis device according to the present invention is illustrated in FIG. 1.

The general geometry of this casing may be the object of many alternative embodiments and will therefore not be described in detail in the following.

Preferably, this casing comprises a metal case 10 in order to form a shield around the electromagnetic sensor according to the invention with respect to the external environment.

As shown earlier, this case defines a cavity or channel 20, the lower portion 22 of which has concavity directed upwards, designed so as to receive a container to be analyzed and to guarantee accurate positioning of the latter relatively to the electromagnetic field emitting/receiving means according to the invention.

Still more specifically, within the scope of the present invention, the aforementioned cavity 20 is formed with a channel of constant cross-section, the generatrices of which are tilted downwards away from the open front face 12 through which a container is introduced.

The rear face of this cavity or channel 20 is closed in order to prevent the analyzed container from sliding on the bottom 22.

The cross-section of the channel 20 may be the object of many alternatives. A first embodiment is illustrated in FIG. 1, according to which the channel 20 has a cross-section with a lock hole shape comprising a cylindrical central portion extended with two diametrically opposite protrusions with a globally rectangular contour. The advantages of the different cross-section alternatives will be explained in the following.

An alternative embodiment is illustrated in FIG. 4, according to which the channel 20 has a circular cross-section. Another alternative embodiment is illustrated in the appended FIG. 5, according to which the channel 20 has a square, or even rectangular cross-section, the diagonals of which are respectively vertical and horizontal so that one edge coincides with the lowest point of the channel 20.

As is seen on the appended FIGS. 1, 4 and 5, the casing 10 preferably further includes a control console 30 fitted with an input and/or programming keyboard, a display device and network-presence and alarm signalling (light and/or sound) means. In this respect, the invention is of course not limited to particular embodiments illustrated in the appended figures.

Preferably, the cavity 20 is coated with a plastic protective coat.

As illustrated in FIG. 2, wherein a container to be analyzed is schematized under reference R and wherein the bottom 22 of the cavity 20 is again found, preferably the electromagnetic sensor(s) intended for measuring the complex dielectric characteristics of the bottle R and of its contents is(are) placed around the cavity 20.

These electromagnetic field emitting/receiving means are preferably formed with one or more transducers 40 (antennas), connected via a connecting network, an electromagnetic measurement network 56 and buses 57, 58, to a generator 50 designed for emitting an electromagnetic wave. Typically the generator 50 is adapted to cover the frequency range from a few Hz, for example 5 Hz, to a few GHz, for example 20 or 50 GHz. The generator 50 is either applied manually by an operator when the latter introduces a container R into the channel 20, or automatically under the action of a sensor 52 designed for detecting the presence of a container R in the channel 20.

Moreover the means 50 are designed in order to measure the complex impedance of the emitting means 40 influenced by the load formed by the container R and its contents, representative of the complex dielectric characteristics of this container R and of its contents. More specifically, the means 50 are designed in order to measure this complex impedance at several sampled frequencies over the aforementioned excitation range from a few Hz to several GHz. Typically, the means 50 thus operate over a number of frequencies between 10 and 50, advantageously over about thirty frequencies.

Moreover, the means 50 are adapted in order to provide a piece of information related to the measured complex impedance and to the nature of the contents of the accordingly detected container.

Preferably, these means 50 are adapted in order to compare the thereby measured complex impedance with predetermined reference values for the same range of frequencies and to generate an alarm when the measured complex impedance deviates from the reference values.

A memory 60 coupled with analysis means 50 via a communications bus 62 is illustrated in FIG. 2, and in which predetermined reference values over the working frequency range may be stored. Moreover, alarm means, preferably present on the control console 30, connected to the means 50 via a communications bus 72 and adapted for generating a sound and/or visual alarm when the measured complex impedance deviates from the reference values, are illustrated in the same FIG. 2 under reference 70.

Alternatively, the reference values may be computed by the means 50 and not contained in a memory 60.

Moreover, according to another alternative, the means 70 may be adapted in order to directly indicate the nature of the contents of the container R or at least the family of these contents instead of or as an addition to the aforementioned alarm means.

The electromagnetic field emitting/receiving means 40 may be the object of many embodiments.

FIG. 6 illustrates a first embodiment wherein these means 40 are formed with a simple winding 42 forming the emitter and the receiver, connected via a two-wire network 54 to the means 56.

FIG. 7 illustrates a second embodiment wherein the means 40 are formed with two windings 43, 44 respectively and if need be alternately forming the emitter and the receiver, connected via a four-wire network 54 to the means 56.

FIG. 8 illustrates a third embodiment wherein the means 40 are formed with two frames 45, 46 with a capacitance surrounding the cavity 20 intended for receiving the container R and connected via a two-wire network 54 to the means 56.

FIG. 9 illustrates an alternative to FIG. 8 wherein the means 40 comprise two capacitances consisting of four frames 45, 46, 47, 48 connected via a four-wire network 54 to the means 56 and respectively and if need be, alternately forming the emitter and the receiver.

FIGS. 10a, 10b, 10c represent another alternative embodiment according to which the means 40 are formed with transmission lines. Typically, these transmission lines operate in the microwave domain. They may be formed with bifilar lines or waveguides with slits.

Moreover, within the scope of the present invention, as illustrated in FIGS. 11a and 11b, sensors simultaneously applying an inductive transducer 42 and a capacitive transducer 45, 46 may be used. With this arrangement, it is possible to reveal that the increase in the real part of the complex dielectric constant is due to a metal frame internal to the container and not to liquid(s) having particular properties. With this arrangement it is thereby possible to reveal the presence of metal screens capable of forming a shield which perturbs the measurement. The inductive sensor 42 powered by an alternating current source will in this case produce eddy currents in the metal portion. These currents will be measured by the processing device. And comparison of the signals from the electric field transducer 45, 46 and from the magnetic field transducer 42 provides satisfactory detection.

Of course, the number of means making up the emitters and/or receivers is by no means limited and may be larger than those illustrated in the appended figures.

One skilled in the art will understand upon reading the foregoing detailed description that the present invention thereby proposes a high frequency sweep electromagnetic sensor with which the dielectric characteristics of the bottle R and of its contents may be measured.

As soon as the object R to be analyzed is positioned in the cavity 20, the generator 50 is either enabled manually or automatically, and the complex impedance of the network formed by the emitting/receiving circuit 40 is influenced by the container R and its contents and measured.

The measured impedance depends on the emitting/receiving circuit and on the load represented by the examined bottle. This complex impedance consists of a real part, related to losses (conductivity) in the analyzed object R and of an imaginary part, related to the dielectric characteristics.

The measurement of the impedance is carried out at different frequencies in the determined range.

All drinkable water-based liquids, such as non-alcoholic beverages, wine and liquors may be well identified by their polar dielectric characteristics, with a high dielectric constant and losses located between a minimum and predetermined value. A different value from the typical one of drinkable liquids will therefore be detected and cause an acoustic and/or visual alarm, plus if necessary possible messages on the display device, or even according to the retained alternative, directly the indication of the nature of the detected contents.

As described earlier, the cross-section of channel 20 may be the object of many alternatives. For example, the cross-section may be shaped as a lock hole as illustrated in FIG. 1, the cross-section may also be of circular shape as illustrated in FIG. 4, or a square or even rectangular shape (with vertical and horizontal diagonals) as illustrated in FIG. 5.

For certain geometries of the cross-section of the channel, the measured complex impedance may vary according to the volume of the container in which a same analyzed liquid is contained.

Figure 12A:
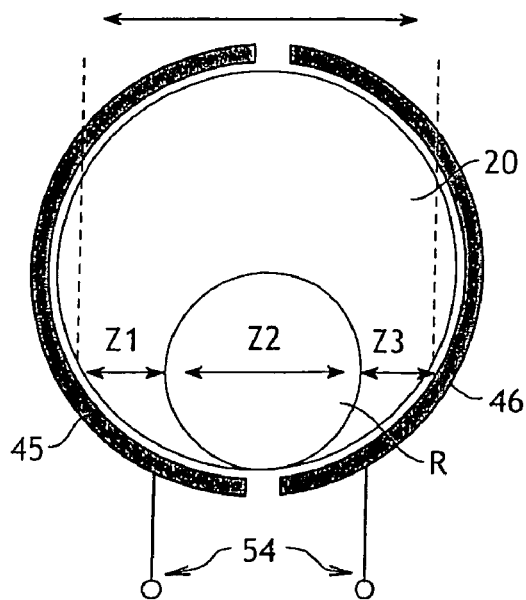
Figure 12B:
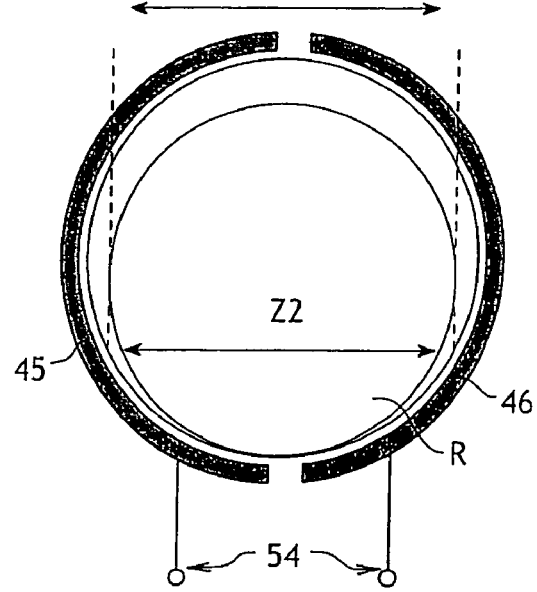

Thus, in the case of a channel 20, the cross-section of which is of a circular shape, as illustrated in FIGS. 12a and 12b, the measured complex impedance $Z_{measured}$ for a container R of 50 centiliters containing water (FIG. 12a) will be different from the measured complex impedance $Z_{measured}$ for a container R of 2 liters containing water (FIG. 12b).

This is due to the fact that the measured complex impedance $Z_{measured}$ corresponds to the equivalent complex impedance $Z_{equivalent}$ of the whole of the dipoles located between the frames 45, 46 of the electromagnetic field emitting/receiving means.

A device comprising a channel 20 with a circular shaped cross-section especially suitable for measuring the complex impedance of the contents of a cylindrical bottle of 2 liters, i.e., a channel 20, the diameter of the cross-section of which is slightly larger than the diameter of a cylindrical bottle of 2 liters, is illustrated in FIGS. 12a and 12b.

As illustrated in FIG. 12a, when this device is used with a container R of 50 centiliters positioned in the channel 20 so that its longitudinal axis of the container R is substantially horizontal, the measured complex impedance $Z_{measured}$ is equal to the sum of the complex impedance $Z_2$ of the water contained in the container R and of the complex impedances $Z_1$ and $Z_3$ of the air located between the walls of the container R and the frames 45, 46.

The complex impedances $Z_1$ and $Z_3$ of the air located between the walls of the container R and the frames 45, 46 are considered as parasitic impedances which should be minimized so that the measured complex impedance is substantially equal to the complex impedance of the liquid contained in the container to be analyzed.

As illustrated in FIG. 12b, when this device is used with a 2 liter container, for which the cross-section is especially suitable, the measured complex impedance $Z_{measured}$ is substantially equal to the complex impedance $Z_2$ of the water contained in the container R.

Indeed, with a 2 liter container for which the cross-section is especially suitable, the parasitic impedances $Z_1$ and $Z_3$ become negligible because the distances between the walls of the container R and the frames 45, 46 are small.

The square (or rectangular) and lock hole geometries of the cross-section have the advantage of making the measurement of the complex impedance independent of the volume of the container in which the liquid to be analyzed is contained.

Indeed, with these geometries, it is possible to limit the distance between the walls of the container R and the frames 45, 46 of the electromagnetic field emitting/receiving means, regardless of the volume of the container R.

Figure 13A:
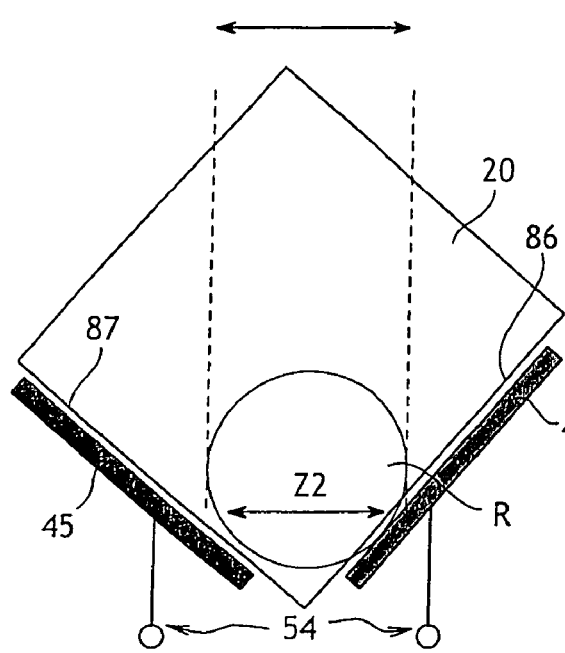
Figure 13B:
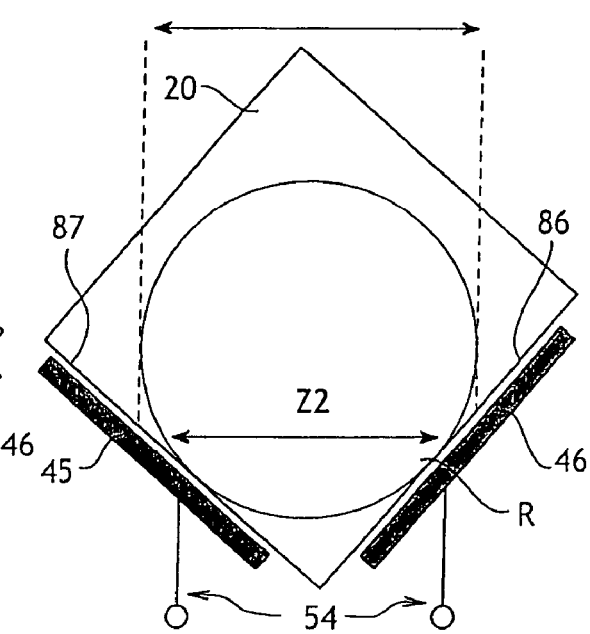

A device according to the present invention comprising a channel with a square-shaped cross-section, the diagonals of which are respectively vertical and horizontal, so that one edge coincides with the lowest point of the channel 20, is illustrated in FIGS. 13a, 13b.

In the case of a container R with a cylindrical shape placed in the channel 20 so that the longitudinal axis of the container R is horizontal, the container R will tend to enter into contact with the partitions 86, 87 of the channel 20 because of gravity, as illustrated in FIGS. 13*a* and 13*b*.

Thus, the distance between the walls of the container and the frames 45, 46 (which are very close to the partitions 86, 87 of the channel 20) is quasi-zero regardless of the diameter of the container containing the liquid to be analyzed, so that the parasitic impedances $Z_1$ and $Z_3$ of the air located between the walls of the container R and the frames are negligible. The measured impedance $Z_{measured}$ is substantially equal to the complex impedance of the liquid contained in the container R regardless of the volume of the container R used.

In the same way as for a channel with a square cross-section, a lock hole cross-section geometry allows the distance to be minimized between the walls of the container containing the liquid to be analyzed and the frames of the device regardless of the volume of the container R used, so that the measurement of the complex impedance is independent of the volume of the container in which the liquid to be analyzed is contained. Thus, in the case of a cylindrical 50 cl container, the latter is positioned between the lower protrusions of the lock-hole shaped cross-section (the distance between these protrusions may be provided as slightly larger than the diameter of a 50 centiliter cylindrical bottle of a standard type). In the case of a 2 liter container, the latter is positioned at the cylindrical central portion of the lock-hole shaped channel.

Thus, the channel 20 of the device preferentially defines a concavity 22 directed upwards. Even more preferentially, the convergence of the partitions 86, 87 of the channel 20 is determined so that not only the distance between the lowest point of the channel 20 and the centre of gravity of the container increases according to the volume of the container R but further the contact point of the container R on the walls of the channel 20 rises and the height of the base of the container relatively to the lowest point of the channel 20 also increases depending on the volume of the container R. Even more preferentially, the concavity 22 directed upwards is obtained by means of two rectilinear sections so as to minimize the effect of parasitic impedances $Z_1$ and $Z_3$ of the air located between the walls of the container R and the partitions 86, 87 of the channel 20.

Of course, the present invention is not limited to the particular embodiments which have just been described but extends to any alternative in accordance with its spirit.

Moreover, it will be noted that within the scope of the present invention, the sensors 40 are preferably adapted in order to cover at least a substantial portion of the containers, or even the totality of the latter. This guarantees a high security level in the analysis, as this allows the entirety of the contents of the containers to be analyzed and not only a portion of the latter.

When a single transducer is provided, the latter is an emitter and receiver, simultaneously or successively.

When several transducers are provided, all the combinations are possible, i.e., these transducers may simultaneously or successively be an emitter and/or receiver.

According to another advantageous feature, the analysis device according to the present invention further comprises a ionizing or radioactive radiation detector assembly. This assembly is intended for detecting the possible presence of traces of radioactive products in the analyzed container.

The ionizing or radioactivity radiation detector assembly may be the object of many embodiments. It may be formed with all the structures known to one skilled in the art, in particular any structure capable of converting a detected ionizing ray into a utilizable electric signal. For example and in a non-limiting way, this may be a Geiger type detector comprising a tube or chamber which accommodates a gas, the composition of which is selected in order to generate a ionizing discharge upon detecting active radiation, and from there an electrical pulse. This may also be a scintillation detector capable of converting the detected energy into light scintillations subsequently converted into an electrical signal by a network of photomultipliers. Many scintillators have been proposed for this purpose, for example those based on sodium iodide, cesium iodide or bismuth germanate.

The ionizing radiation detector assembly is placed in any suitable location and preferably in immediate proximity to the walls of the cavity 20, on the outside of the latter. An a priori optimum localization of this assembly, under the cavity 20 against both walls forming the lower dihedron of the cavity 20 is illustrated in FIG. 8, under reference 100, 110.

The ionizing radiation detector assembly 100, 110 is adapted in order to operate in masked time, in parallel with the complex impedance measuring device described earlier. The ionizing radiation detector assembly 100, 110 is controlled and put into service by any suitable means detecting the presence of a container in the cavity. Preferably, but in a non-limiting way, the ionizing radiation detector assembly is thus initiated by a signal sampled on the complex impedance measuring chain and representative of the presence of such a container in the channel 20.

Several embodiments of means 40 forming electromagnetic field emitters/receivers have been described earlier. Within the scope of the present invention, means are preferably provided which allow the configuration of the emitter-forming means and the receiver-forming means to be changed, in order to enrich the available information, for example on the volume of the analyzed container.

In particular, an embodiment has been illustrated in FIG. 9, according to which the means 40 comprise four capacitive frames 45, 46, 47 and 48 respectively positioned on the outside of each of the four faces of a square section of the channel 20. In this context, switching means within the measuring network 56 are preferably provided for changing the configuration of the means 40 so that in a first configuration, one of the two lower frames 46 or 48 forms an emitter whereas the other lower frames 48 or 46 forms a receiver, and a second configuration in which both lower frames 46 and 48 form emitters whereas both upper frames 45 and 47 form receivers, or vice versa.

The invention claimed is:

1. A device for analyzing the composition of the contents of a container comprising:
    a channel (20) for receiving a container, which channel comprises a lower portion tilted downwards away from an open front face of the channel through which a container is introduced so as to define a concavity directed upwards, and
    non-destructive analysis means (40, 50) associated with this channel, wherein the non-destructive analysis means (40, 50) comprise:
    means (40) for emitting/receiving an electromagnetic field at least at several frequencies comprised in a determined frequency range,
    means (50) capable of measuring the complex impedance of emitting/receiving means influenced by the load formed by the container (R) and its contents, representative of the complex dielectric characteristics of the container and of its contents, and
    means (50) capable of providing a piece of information related to the measured complex impedance and consequently, to the nature of the contents of said container.

2. The device according to claim 1, wherein the means capable of comparing the measured complex impedance are adapted in order to compare the latter with reference values contained in a memory (60).

3. The device according to claim 1, wherein the means (50) capable of providing a piece of information comprise means capable of comparing the measured complex impedance with predetermined reference values for the same frequency range and of generating an alarm when the measured complex impedance deviates from the reference values.

4. The device according to claim 1, wherein the means (50) capable of providing information related to the measured complex impedance comprise means (70) capable of indicating the thereby detected nature of the contents of the container or at least a family of these contents.

5. The device according to claim 1, wherein the electromagnetic field emitting/receiving means (40) are adapted for sweeping the range of frequencies from a few Hz to a few GHz.

6. The device according to claim 1, wherein the means (50) capable of measuring the complex impedance are adapted in order to measure the latter over a plurality of sampled frequencies over the range covered by the emitting/receiving means.

7. The device according to claim 1, further comprising:
a sensor (52) adapted in order to detect the placing of a container (R) in the channel (22).

8. The device according to claim 1, further comprising manual actuation means adapted for initiating the putting into service of means (40) for emitting/receiving an electromagnetic field.

9. The device according to claim 1, wherein the device is placed in a metal case (10).

10. The device according to claim 1, wherein convergence of partitions (86, 87) of the channel (20) is determined so that the distance between a lowest point of the channel (20) and a centre of gravity of the container (R) increases according to the volume of the container (R).

11. The device according to claim 1, wherein the channel (20) defines a concavity (22) directed upwards, obtained by means of two rectilinear sections.

12. The device according to claim 1, wherein convergence of partitions (86, 87) of the channel (20) is adapted in order to suppress parasitic complex impedances defined laterally between the walls of the container and the partitions (86, 87) of the supporting means (20).

13. The device according to claim 1, wherein convergence of partitions (86, 87) of the channel (20) is determined so that a contact point of the container (R) on the walls of the supporting means (20) rises according to the volume of the container (R).

14. The device according to claim 1, wherein a height of a base of the container (R) relatively to a lowest point of the channel (20), increases according to the volume of the container (R).

15. The device according to claim 1, wherein the means (40) for emitting/receiving an electromagnetic field are of the inductive type.

16. The device according to claim 1, wherein the means (40) for emitting/receiving an electromagnetic field are of the capacitive type.

17. The device according to claim 1, wherein the means (40) for emitting/receiving an electromagnetic field are formed with transmission lines.

18. The device according to claim 1, wherein the emitting/receiving means (40) simultaneously apply an inductive transducer (42) and a capacitive transducer (45, 46).

19. The device according to claim 1, wherein the device further comprises an ionizing or radioactive radiation detector assembly (100, 110).

20. The device according to claim 19, wherein the ionizing radiation detector assembly (100, 110) is placed in immediate proximity to the container-supporting means (20) on the outside of the latter.

21. The device according to claim 19, wherein the ionizing radiation detector assembly (100, 110) is adapted for working in masked time, in parallel with a complex impedance measuring device.

22. The device according to claim 19, wherein the ionizing radiation detector assembly (100, 110) is controlled and put into service by a signal sampled on the complex impedance measuring chain and representative of the presence of a container on the container-supporting means (20).

23. The device according to claim 1, wherein the device comprises means for changing the configuration of an emitter-forming means and receiver-forming means.

24. The device according to claim 1, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

25. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein convergence of partitions (86, 87) of the channel (20) is determined so that the distance between a lowest point of the channel (20) and a centre of gravity of the container (R) increases according to the volume of the container (R).

26. The device according to claim 25, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

27. The device according to claim 26, wherein the electromagnetic field emitting/receiving means (40) are adapted for sweeping the range of frequencies from a few Hz to a few GHz.

28. The device according to claim 25, wherein convergence of partitions (86, 87) of the channel (20) is determined so that a contact point of the container (R) on the walls of the supporting means (20) rises according to the volume of the container (R).

29. The device according to claim 25, wherein the device further comprises an ionizing or radioactive radiation detector assembly (100, 110).

30. The device according to claim 25, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

31. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein the channel (20) defines a concavity (22) directed upwards, obtained by means of two rectilinear sections.

32. The device according to claim 31, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

33. The device according to claim 32, wherein the electromagnetic field emitting/receiving means (40) are adapted for sweeping the range of frequencies from a few Hz to a few GHz.

34. The device according to claim 31, wherein convergence of partitions (86, 87) of the channel (20) is determined so that a contact point of the container (R) on the walls of the supporting means (20) rises according to the volume of the container (R).

35. The device according to claim 31, wherein the device further comprises an ionizing or radioactive radiation detector assembly (100, 110).

36. The device according to claim 31, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

37. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein convergence of partitions (86, 87) of the channel (20) is adapted in order to suppress parasitic complex impedances defined laterally between the walls of the container and the partitions (86, 87) of the supporting means (20).

38. The device according to claim 37, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

39. The device according to claim 38, wherein the electromagnetic field emitting/receiving means (40) are adapted for sweeping the range of frequencies from a few Hz to a few GHz.

40. The device according to claim 37, wherein convergence of partitions (86, 87) of the channel (20) determined so that a contact point of the container (R) on the walls of the supporting means (20) rises according to the volume of the container (R).

41. The device according to claim 37, wherein the device further comprises an ionizing or radioactive radiation detector assembly (100, 110).

42. The device according to claim 37, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

43. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein convergence of partitions (86, 87) of the channel (20) is determined so that a contact point of the container (R) on the walls of the supporting means (20) rises according to the volume of the container (R).

44. The device according to claim 43, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and means (50) capable of providing a piece of information related to the measured complex impedance and consequently, to the nature of the contents of said container.

45. The device according to claim 44, wherein the electromagnetic field emitting/receiving means (40) are adapted for sweeping the range of frequencies from a few Hz to a few GHz.

46. The device according to claim 43, wherein the device further comprises an ionizing or radioactive radiation detector assembly (100, 110).

47. The device according to claim 43, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

48. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein the device further comprises an ionizing or radioactive radiation detector assembly (100, 110).

49. The device according to claim 48, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

50. The device according to claim 48, wherein the electromagnetic field emitting/receiving means (40) are adapted for sweeping the range of frequencies from a few Hz to a few GHz.

51. The device according to claim 48, wherein convergence of partitions (86, 87) of the channel (20) is determined so that a contact point of the container (R) on the walls of the supporting means (20) rises according to the volume of the container (R).

52. The device according to claim 48, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

53. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein the device comprises means for changing the configuration of the emitter-forming means and receiver-forming means.

54. The device according to claim 53, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

55. A device for analyzing the composition of the contents of a container comprising:
a channel (20) for receiving a container, which channel comprises a lower portion tilted downwards away from an open front face of the channel through which a container is introduced so as to define a concavity directed upwards, and
non-destructive analysis means (40, 50) associated with this channel, wherein the non-destructive analysis means include emitting/receiving means (40) which comprise four capacitive frames (45, 46, 47 and 48) respectively positioned on the outside of each of four faces of a square section of a channel (20) for receiving a container and that switching means are provided for changing the configuration of non-destructive analysis means (40) so that in a first configuration, one of the two lower frames (46 or 48) forms an emitter whereas the other lower frame (48 or 46) forms a receiver and a second configuration in which both lower frames (46 and 48) form emitters whereas both upper frames (45 and 47) form receivers, or vice versa.

56. The device according to claim 55, wherein the non-destructive analysis means (40, 50) comprise:
means (40) for emitting/receiving an electromagnetic field at least at several frequencies comprised in a determined frequency range,
means (50) capable of measuring the complex impedance of emitting/receiving means influenced by the load formed by the container (R) and its contents, representative of the complex dielectric characteristics of the container and of its contents, and
means (50) capable of providing a piece of information related to the measured complex impedance and consequently, to the nature of the contents of said container.

* * * * *